(12) United States Patent
Gagner

(10) Patent No.: US 12,246,100 B2
(45) Date of Patent: Mar. 11, 2025

(54) NATURAL FIBERS HAVING ABSORBABLE AND HYDROPHOBIC PROPERTIES FOR MAKING SURGICAL SUTURES AND SURGICAL MESHES

(71) Applicant: BALLAST MEDICAL INC., Montréal (CA)

(72) Inventor: Michel Gagner, Montréal (CA)

(73) Assignee: Ballast Medical, Inc., Montreal (CA)

( * ) Notice: Subject to any disclaimer, the term of this patent is extended or adjusted under 35 U.S.C. 154(b) by 0 days.

(21) Appl. No.: 18/656,580

(22) Filed: May 6, 2024

(65) Prior Publication Data

US 2025/0001039 A1    Jan. 2, 2025

Related U.S. Application Data

(60) Provisional application No. 63/585,317, filed on Sep. 26, 2023, provisional application No. 63/511,043, filed on Jun. 29, 2023.

(51) Int. Cl.
*A61L 17/06*    (2006.01)
*A61L 17/00*    (2006.01)
*A61L 17/14*    (2006.01)

(52) U.S. Cl.
CPC ............. *A61L 17/06* (2013.01); *A61L 17/005* (2013.01); *A61L 17/145* (2013.01)

(58) Field of Classification Search
CPC ....... A61L 17/005; A61L 17/06; A61L 17/145
See application file for complete search history.

(56) References Cited

U.S. PATENT DOCUMENTS

| 2,292,500 A | 8/1942 | Watts |
| 7,905,903 B2 | 3/2011 | Stone et al. |
| 2012/0197295 A1 | 8/2012 | Yoshikawa et al. |

FOREIGN PATENT DOCUMENTS

| CA | 2604870 A1 | 10/2006 |
| WO | 2020247594 A1 | 12/2020 |

OTHER PUBLICATIONS

Ramadoss et al., "Drug Eluting Bioresorbable Cellulose Acetate/PEO/HPMC Composite With Propolis Extracts for Suturing Application". Journal of Materials Science and Surface Engineering, Oct. 21, 2021 (Oct. 21, 2021), vol. 8(2), pp. 1010-1020.

(Continued)

*Primary Examiner* — Ryan J. Severson
(74) *Attorney, Agent, or Firm* — Andrew H. Berks

(57) ABSTRACT

Suture materials for producing medical devices are provided. The suture materials can include natural fibers, and can be suitable for making multifilament sutures and surgical meshes comprising multifilament sutures as examples of medical devices. The multifilament suture can include a plurality of filaments combined together according to a twined pattern, and at least one filament of the plurality of filaments can include natural fibers, synthetic fibers, or mineral-based fibers. A suture device can include the multifilament suture combined with a suture needle. The multifilament suture can be coated with a biocompatible coating, such as a bioactive agent, and/or include a first set of filaments that includes natural fibers and a second set of filaments that includes natural fibers that are different from the natural fibers of the first set of filaments, synthetic fibers or mineral-based fibers, for instance.

22 Claims, 4 Drawing Sheets

(56) References Cited

OTHER PUBLICATIONS

Guambo et al., "Natural Cellulose Fibers for Surgical Suture Applications". Polymers, Dec. 18, 2020 (Dec. 18, 2020), vol. 12(12), pp. 3042.
Twisted linen. Vital Sutures (n.d.). https://vitalsutures.com/product/twisted-linen/ (page capture enclosed).
Liu et al. "New surgical meshes with patterned nanofiber mats" RSC Advances, Jun. 5, 2019, pp. 17679-17690. vol. 9 Issue 31, The Royal Society of Chemistry, http://dx.doi.org/10.1039/C9RA01917K.
International Search Report PCT/CA2024/050622 (corresponding PCT application).
Written opinion of the international search authority PCT/CA2024/050622 (corresponding PCT application).

NATURAL FIBERS HAVING ABSORBABLE AND HYDROPHOBIC PROPERTIES FOR MAKING SURGICAL SUTURES AND SURGICAL MESHES

TECHNICAL FIELD

The technical field relates to medical devices for treating damaged tissues, such as surgical suture and surgical meshes. More particularly, the technical field relates to natural fibers for making surgical sutures and surgical meshes.

BACKGROUND

Surgical sutures and surgical meshes are medical devices that can be used in a broad range of surgical procedures. For instance, surgical sutures can be used to approximate portions of biological tissue after such tissue has been subjected to an injury or surgery, which in turn can facilitate natural healing processes to occur. Surgical meshes can be used as tissue scaffolds or structural supports to encourage growth of new biological tissue at a target tissue site in a patient to occlude an opening in an organ wall or to repair a tendon or a hernia, for instance.

Surgical sutures and surgical meshes are generally made from biocompatible materials, such as synthetic and natural biocompatible materials, which may be non-absorbable or absorbable physiological conditions. These biocompatible materials can also be further categorized according to whether their physical structure corresponds to a monofilament or a multifilament.

Selection of a suture material for a surgical suture or a surgical mesh for a given surgical procedure can be made according to various factors, including the tensile strength of the suture material, its ability to resist infection, the friction it generates, the inflammatory response it may trigger, etc. For instance, in the case of surgical sutures, the surgical material can typically be selected to enable the approximation of healthy tissue edges with minimal tension, ideally no contamination or infection, and adequate blood supply.

However, while surgical materials currently available may perform sufficiently well in certain clinical scenarios, each of these currently available surgical materials also has drawbacks that may impair the healing processes that should be taking place. For instance, surgical materials that are provided as multifilament are generally stronger than those provided as monofilaments, but multifilament can also generate high friction and tissue-drag when passing through the tissues, resulting in additional trauma. Furthermore, interstices defined between adjacent filaments of multifilament sutures can increase the capillarity of the multifilament sutures and provide ideal locations to harbour bacteria, which may lead to higher risks of infections. Although multifilament sutures can be treated with a coating to counteract these drawbacks, these coatings are known to undesirably decrease knot security.

Accordingly, there remain a number of challenges with respect to surgical sutures and surgical meshes, and in particular, challenges related to the selection of surgical materials for preparing surgical sutures and surgical meshes.

SUMMARY

In accordance with an aspect, there is provided a multifilament suture for use as a surgical suture, the multifilament suture comprising:

a plurality of filaments combined together according to a twined pattern, at least one filament of the plurality of filaments comprising natural fibers, the natural fibers being both absorbable and hydrophobic at physiological conditions.

In some implementations, the natural fibers of the at least one filament are absorbable by proteolysis and/or hydrolysis.

In some implementations, the at least one filament of the plurality of filaments is configured to prevent bacterial adhesion in an interstice defined between adjacent filaments of the plurality of filaments.

In some implementations, the natural fibers comprise cellulosic plant fibers.

In some implementations, the cellulosic plant fibers comprise milkweed fibers.

In some implementations, the milkweed fibers include one or more of *Asclepias syriaca* fibers and *Asclepias speciosa* fibers.

In some implementations, the plurality of filaments further comprises additional natural fibers that are different from the milkweed fibers.

In some implementations, the additional natural fibers comprise cellulosic plant fibers.

In some implementations, the additional natural fibers comprise one or more of kapok fibers, bamboo fibers, linen fibers, cotton fibers, abacá fibers, acetate fibers, banana fibers, coir fibers, flax fibers, hemp fibers, jute fibers, kenaf fibers, lyocell fibers, modal fibers, piña fibers, raffia fibers, ramie fibers, rayon fibers, sisal fibers, and soy protein fibers.

In some implementations, the additional natural fibers comprise animal fibers.

In some implementations, the additional natural fibers comprise one or more of spider silk fibers, wool fibers, alpaca fibers, angora wool fibers, azlon fibers, byssus fibers, camel hair fibers, cashmere wool fibers, chiengora fibers, lambswool fibers, llama fibers, mohair wool fibers, qiviut fibers, rabbit fibers, silk fibers, eri silk fibers, vicuña fibers, and yak fibers.

In some implementations, the plurality of filaments further comprises synthetic fibers.

In some implementations, the synthetic fibres comprise one or more of acrylic fibers, Kevlar™ fibers, modacrylic fibers, Nomex™ fibers, nylon fibers, polyester fibers, spandex fibers, and rayon fibers.

In some implementations, the synthetic fibres are absorbable synthetic fibers.

In some implementations, the absorbable synthetic fibers comprise one or more of polyglactin, lactides, polyglycolic acid, polylactic acid, glycolide, p-dioxanone, epsilon-caprolactone, and trimethylene carbonate.

In some implementations, the plurality of filaments further comprises mineral-based fibers.

In some implementations, the mineral-based fibers comprise one or more of glass fibers, and fiberglass fibers.

In some implementations, the filaments of the plurality of filaments are braided or interlaced according to the twined pattern.

In some implementations, the twined pattern is a one over one twined pattern.

In some implementations, the twined pattern is a one over two twined pattern.

In some implementations, the twined pattern is a two over two twined pattern.

In some implementations, the twined pattern defines a core and a braided sheath provided around the core.

In some implementations, the filaments of the plurality of filaments are combined together to form yarns, and the braided sheath comprises braided yarns.

In some implementations, the multifilament suture further comprises a biocompatible coating provided onto an external surface of the multifilament suture.

In some implementations, the biocompatible coating is configured to reduce tissue-drag of the multifilament suture.

In some implementations, a thickness of the biocompatible coating is at least a quarter of an average diameter of the filaments of the plurality of filaments.

In some implementations, the thickness of the biocompatible coating is at least a half of the average diameter of the filaments of the plurality of filaments.

In some implementations, the biocompatible coating comprises an absorbable polymer.

In some implementations, the biocompatible coating comprises a bioactive agent having therapeutic properties.

In some implementations, the bioactive agent comprises one or more of a cell growth promoter, a cell growth inhibitor, an antibiotic, a cytokine, a healing promoter, a clotting modulator, an anti-inflammatory, and an anti-scarring agent.

In some implementations, the multifilament suture has a diameter between about 0.01 mm and about 0.7 mm.

In some implementations, the multifilament suture has a diameter between about 0.1 mm and about 0.5 mm.

In accordance with another aspect, there is provided a surgical mesh for implantation at a surgical site, the surgical mesh comprising:
  a plurality of multifilament sutures each comprising filaments, the plurality of multifilament sutures being combined together according to a mesh pattern, at least one filament of the plurality of multifilament sutures comprising natural fibers, the natural fibers being both absorbable and hydrophobic at physiological conditions.

In some implementations, the natural fibers of the at least one filament are absorbable by proteolysis and/or hydrolysis.

In some implementations, the at least one filament is configured to prevent bacterial adhesion in an interstice defined between adjacent filaments.

In some implementations, the natural fibers comprise cellulosic plant fibers.

In some implementations, the cellulosic plant fibers comprise milkweed fibers.

In some implementations, the milkweed fibers include one or more of *Asclepias syriaca* fibers and *Asclepias speciosa* fibers.

In some implementations, the plurality of filaments further comprises additional natural fibers that are different from the milkweed fibers.

In some implementations, the additional natural fibers comprise cellulosic plant fibers.

In some implementations, the additional natural fibers comprise one or more of kapok fibers, bamboo fibers, linen fibers, cotton fibers, abacá fibers, acetate fibers, banana fibers, coir fibers, flax fibers, hemp fibers, jute fibers, kenaf fibers, lyocell fibers, modal fibers, piña fibers, raffia fibers, ramie fibers, rayon fibers, sisal fibers, and soy protein fibers.

In some implementations, the additional natural fibers comprise animal fibers.

In some implementations, the additional natural fibers comprise one or more of spider silk fibers, wool fibers, alpaca fibers, angora wool fibers, azlon fibers, byssus fibers, camel hair fibers, cashmere wool fibers, chiengora fibers, lambswool fibers, llama fibers, mohair wool fibers, qiviut fibers, rabbit fibers, silk fibers, eri silk fibers, vicuña fibers, and yak fibers.

In some implementations, the plurality of filaments further comprises synthetic fibers.

In some implementations, the synthetic fibres comprise one or more of acrylic fibers, Kevlar™ fibers, modacrylic fibers, Nomex™ fibers, nylon fibers, polyester fibers, spandex fibers, and rayon fibers.

In some implementations, the synthetic fibres are absorbable synthetic fibers.

In some implementations, the synthetic fibers are one or more of polyglactin, lactides, polyglycolic acid, polylactic acid, glycolide, p-dioxanone, epsilon-caprolactone, and trimethylene carbonate.

In some implementations, the plurality of filaments further comprises mineral-based fibers.

In some implementations, the mineral-based fibers comprise one or more of glass fibers, and fiberglass fibers.

In some implementations, the surgical mesh defines a porous matrix configured to promote tissue growth at the surgical site.

In some implementations, the mesh pattern comprises a woven pattern, a knitted pattern, a warp-knitted pattern or a nonwoven pattern.

In some implementations, the surgical mesh is configured as a corrugated surgical mesh.

In some implementations, the surgical mesh further comprises a non-mesh material, the combination of the surgical mesh and the non-mesh material forming a surgical scaffold configured to provide support for tissue surrounding the surgical site.

In accordance with another aspect, there is provided a suture device for approximating portions of a biological soft tissue, the suture device comprising:
  a multifilament suture comprising:
    a plurality of filaments combined together according to a twined pattern, at least one filament of the plurality of filaments comprising natural fibers, the natural fibers being both absorbable and hydrophobic at physiological conditions; and
  a suture needle having a needle point configured for penetrating tissue, and a suture engaging end configured for engagement with the multifilament suture.

In some implementations, the natural fibers of the at least one filament are absorbable by proteolysis and/or hydrolysis.

In some implementations, the at least one filament of the plurality of filaments is configured to prevent bacterial adhesion in an interstice defined between adjacent filaments of the plurality of filaments.

In some implementations, the natural fibers comprise cellulosic plant fibers.

In some implementations, the cellulosic plant fibers comprise milkweed fibers.

In some implementations, the milkweed fibers include one or more of *Asclepias syriaca* fibers and *Asclepias speciosa* fibers.

In some implementations, the plurality of filaments further comprises additional natural fibers that are different from the milkweed fibers.

In some implementations, the additional natural fibers comprise cellulosic plant fibers.

In some implementations, the additional natural fibers comprise one or more of kapok fibers, bamboo fibers, linen fibers, cotton fibers, abacá fibers, acetate fibers, banana fibers, coir fibers, flax fibers, hemp fibers, jute fibers, kenaf fibers, lyocell fibers, modal fibers, piña fibers, raffia fibers, ramie fibers, rayon fibers, sisal fibers, and soy protein fibers.

In some implementations, the additional natural fibers comprise animal fibers.

In some implementations, the additional natural fibers comprise one or more of spider silk fibers, wool fibers, alpaca fibers, angora wool fibers, azlon fibers, byssus fibers, camel hair fibers, cashmere wool fibers, chiengora fibers, lambswool fibers, llama fibers, mohair wool fibers, qiviut fibers, rabbit fibers, silk fibers, eri silk fibers, vicuña fibers, and yak fibers.

In some implementations, the plurality of filaments further comprises synthetic fibers.

In some implementations, the synthetic fibres comprise one or more of acrylic fibers, Kevlar™ fibers, modacrylic fibers, Nomex™ fibers, nylon fibers, polyester fibers, spandex fibers, and rayon fibers.

In some implementations, the synthetic fibres are absorbable synthetic fibers.

In some implementations, the absorbable synthetic fibers comprise one or more of polyglactin, lactides, polyglycolic acid, polylactic acid, glycolide, p-dioxanone, epsilon-caprolactone, and trimethylene carbonate.

In some implementations, the plurality of filaments further comprises mineral-based fibers.

In some implementations, the mineral-based fibers comprise one or more of glass fibers, and fiberglass fibers.

In some implementations, the suture needle comprises a hollow body, and the suture engages end of the suture needle is a swagged end configured to receive an extremity of the multifilament suture within the hollow body of the suture needle in a crimped configuration.

In some implementations, the suture needle comprises one or more of a straight body, a curved body, and a serpentine body.

In accordance with another aspect, there is provided a suture device for approximating portions of a biological soft tissue, the suture device comprising:
  a multifilament suture comprising:
    a plurality of filaments combined together according to a twined pattern, at least one filament of the plurality of filaments comprising natural fibers, the natural fibers being both absorbable and hydrophobic at physiological conditions; and
    a biocompatible coating provided onto a surface of the multifilament suture.

In some implementations, the natural fibers of the at least one filament are absorbable by proteolysis and/or hydrolysis.

In some implementations, the at least one filament of the plurality of filaments is configured to prevent bacterial adhesion in an interstice defined between adjacent filaments of the plurality of filaments.

In some implementations, the natural fibers comprise cellulosic plant fibers.

In some implementations, the cellulosic plant fibers comprise milkweed fibers.

In some implementations, the milkweed fibers include one or more of *Asclepias syriaca* fibers and *Asclepias speciosa* fibers.

In some implementations, the plurality of filaments further comprises additional natural fibers that are different from the milkweed fibers.

In some implementations, the additional natural fibers comprise cellulosic plant fibers.

In some implementations, the additional natural fibers comprise one or more of kapok fibers, bamboo fibers, linen fibers, cotton fibers, abacá fibers, acetate fibers, banana fibers, coir fibers, flax fibers, hemp fibers, jute fibers, kenaf fibers, lyocell fibers, modal fibers, piña fibers, raffia fibers, ramie fibers, rayon fibers, sisal fibers, and soy protein fibers.

In some implementations, the additional natural fibers comprise animal fibers.

In some implementations, the additional natural fibers comprise one or more of spider silk fibers, wool fibers, alpaca fibers, angora wool fibers, azlon fibers, byssus fibers, camel hair fibers, cashmere wool fibers, chiengora fibers, lambswool fibers, llama fibers, mohair wool fibers, qiviut fibers, rabbit fibers, silk fibers, eri silk fibers, vicuña fibers, and yak fibers.

In some implementations, the plurality of filaments further comprises synthetic fibers.

In some implementations, the synthetic fibres comprise one or more of acrylic fibers, Kevlar™ fibers, modacrylic fibers, Nomex™ fibers, nylon fibers, polyester fibers, spandex fibers, and rayon fibers.

In some implementations, the synthetic fibres are absorbable synthetic fibers.

In some implementations, the absorbable synthetic fibers comprise one or more of polyglactin, lactides, polyglycolic acid, polylactic acid, glycolide, p-dioxanone, epsilon-caprolactone, and trimethylene carbonate.

In some implementations, the plurality of filaments further comprises mineral-based fibers.

In some implementations, the mineral-based fibers comprise one or more of glass fibers, and fiberglass fibers.

In some implementations, the biocompatible coating is configured to reduce tissue-drag of the multifilament suture.

In some implementations, the biocompatible coating comprises an absorbable polymer.

In some implementations, the biocompatible coating comprises a bioactive agent having therapeutic properties.

In some implementations, the bioactive agent comprises one or more of a cell growth promoter, a cell growth inhibitor, an antibiotic, a cytokine, a healing promoter, a clotting modulator, an anti-inflammatory, and an anti-scarring agent.

In accordance with another aspect, there is provided a multifilament suture for use as a surgical suture, the multifilament suture comprising:
  a first set of filaments comprising natural fibers, the natural fibers being both absorbable and hydrophobic at physiological conditions; and
  a second set of filaments comprising an absorbable synthetic suture material, the first and second sets of filaments being combined together according to a twined pattern to form the multifilament suture.

In some implementations, the natural fibers of the first set of filaments are absorbable by proteolysis and/or hydrolysis.

In some implementations, the first set of filaments is configured to prevent bacterial adhesion in interstices defined between adjacent filaments of the first set of filaments.

In some implementations, the natural fibers comprise cellulosic plant fibers.

In some implementations, the cellulosic plant fibers comprise milkweed fibers.

In some implementations, the milkweed fibers include one or more of *Asclepias syriaca* fibers and *Asclepias speciosa* fibers.

In some implementations, the synthetic suture material comprises one or more of polyglactin, lactides, polyglycolic acid, polylactic acid, glycolide, p-dioxanone, epsilon-caprolactone, and trimethylene carbonate.

In accordance with another aspect, there is provided a multifilament suture for use as a surgical suture, the multifilament suture comprising:
a plurality of filaments combined together according to a twined pattern, at least one filament of the plurality of filaments comprising milkweed fibers.

In some implementations, the multifilament suture comprises one or more features as defined above.

In accordance with another aspect, there is provided a suture device for approximating portions of a biological soft tissue, the suture device comprising:
a multifilament suture comprising:
a plurality of filaments combined together according to a twined pattern, at least one filament of the plurality of filaments comprising milkweed fibers; and
a suture needle having a needle point configured for penetrating tissue, and a suture engaging end configured for engagement with the multifilament suture.

In some implementations, the multifilament suture comprises one or more features as defined above.

In accordance with another aspect, there is provided a multifilament suture for use as a surgical suture, the multifilament suture comprising:
a first set of filaments comprising natural fibers, the natural fibers being both absorbable and hydrophobic at physiological conditions; and
a second set of filaments comprising one or more of natural fibers that are different from the natural fibers of the first set of filaments, synthetic fibers, and mineral-based fibers, the first and second sets of filaments being combined together according to a twined pattern to form the multifilament suture.

In some implementations, the natural fibers of the first set of filaments are absorbable by proteolysis and/or hydrolysis.

In some implementations, the first set of filaments is configured to prevent bacterial adhesion in interstices defined between adjacent filaments of the first set of filaments.

In some implementations, the natural fibers of the first set of filaments comprise cellulosic plant fibers.

In some implementations, the cellulosic plant fibers comprise milkweed fibers.

In some implementations, the milkweed fibers include one or more of *Asclepias syriaca* fibers and *Asclepias speciosa* fibers.

In some implementations, the natural fibers of the second set of filaments comprise cellulosic plant fibers.

In some implementations, the natural fibers of the second set of filaments comprises one or more of kapok fibers, bamboo fibers, linen fibers, cotton fibers, abacá fibers, acetate fibers, banana fibers, coir fibers, flax fibers, hemp fibers, jute fibers, kenaf fibers, lyocell fibers, modal fibers, piña fibers, raffia fibers, ramie fibers, rayon fibers, sisal fibers, and soy protein fibers.

In some implementations, the natural fibers of the second set of filaments comprise animal fibers.

In some implementations, the natural fibers of the second set of filaments comprise one or more of spider silk fibers, wool fibers, alpaca fibers, angora wool fibers, azlon fibers, byssus fibers, camel hair fibers, cashmere wool fibers, chiengora fibers, lambswool fibers, llama fibers, mohair wool fibers, qiviut fibers, rabbit fibers, silk fibers, eri silk fibers, vicuña fibers, and yak fibers.

In some implementations, the synthetic fibres comprise one or more of acrylic fibers, Kevlar™ fibers, modacrylic fibers, Nomex™ fibers, nylon fibers, polyester fibers, spandex fibers, and rayon fibers.

In some implementations, the synthetic fibres are absorbable synthetic fibers.

In some implementations, the absorbable synthetic fibers comprise one or more of polyglactin, lactides, polyglycolic acid, polylactic acid, glycolide, p-dioxanone, epsilon-caprolactone, and trimethylene carbonate.

In some implementations, the mineral-based fibers comprise one or more of glass fibers, and fiberglass fibers.

BRIEF DESCRIPTION OF THE DRAWINGS

The attached figures illustrate various features, aspects and implementations of the technology described herein.

DETAILED DESCRIPTION

Figure 1:
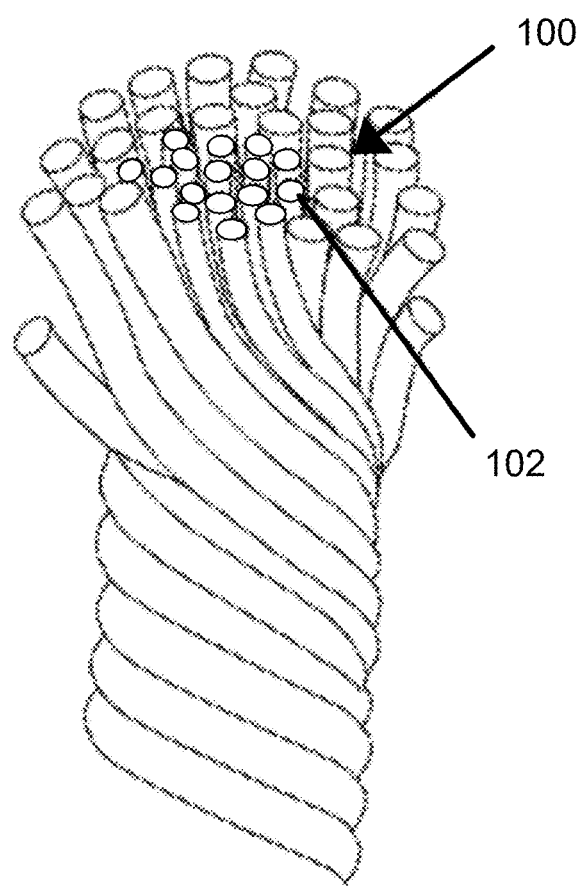
FIG. 1 is a perspective view of a multifilament suture, in accordance with an implementation.

Techniques described herein relate to suture materials for producing medical devices, including surgical sutures and surgical meshes, that can be used in the context of medical procedures such as tissue approximation and tissue repair. The suture materials can include natural fibers having desirable properties, such as being hydrophobic and absorbable at physiological conditions, and can be suitable for making multifilament sutures and meshes comprising multifilament sutures. These desirable properties can in turn provide a suitable biological compatibility and tensile strength. Providing suture materials made of natural fibers that are both absorbable and hydrophobic can have various benefits. For instance, an absorbable suture material can be chosen for ligating tissue that will be inaccessible after implantation, and because they degrade overtime and do not require removal after healing has occurred. A hydrophobic material can enable reducing cellular adhesion, therefore limiting bacterial colonization. Combining these two properties in a single suture material made of natural fibers can thus enable providing a resulting multifilament surgical suture or surgical mesh having a distinct technical profile that can make it suitable for a wide variety of medical applications, including those where risks of infection are high. These medical applications include soft tissue repair such as, for instance, repairing fibrous tissue, such as muscle, ligament or tendon, attaching soft tissue to bone, or any other tissue repair in cardiological, laparoscopic, urological, plastic or other surgical procedures performed on a patient.

As used herein, the expression "natural fiber" refers to a hair-like raw material having a diameter that is negligible in comparison with its length and that is obtainable from a vegetable source. The natural fibers can be spun into filaments, and a given number of filaments can be optionally combined to produce yarns. For instance, the natural fibers can include cellulosic plant fibers. In some implementations and as mentioned above, the natural fibers described herein can be both absorbable and hydrophobic. An example of such natural fibers is milkweed fibers. Milkweed fibers, also referred to as milkweed floss, are vegetable seed fibers obtained from the seeds of milkweed plants (genus *Asclepias*) and other plants of the Asclepiadaceae subfamily. Milkweed fibers typically take the form of soft, lustrous and buoyant fibers having a yellowish or white colour. Individual milkweed fibers can typically have a length between about 1 and 3 cm in length and a mean diameter between about 20 and 50 microns in diameter. The milkweed fibers can have a density being between about 0.10 and about 0.35 g/cm$^3$.

As used herein, the term "absorbable" refers to a material having a tensile strength that is substantially reduced within 60 days following an implantation in tissue, i.e., at physiological conditions, although it is to be understood that the material may subsequently take several additional weeks before being completely absorbed. The absorbable nature of the material stems from its susceptibility to breakdown, decomposition, degradation, resorption and/or dissolution, under the action of biological processes, such as enzymatic reaction and/or hydrolysis. In some instances, an absorbable suture material can be entirely absorbed within several months. In some instances, an absorbable suture material can further be biodegradable and thus capable of being decomposed by bacteria or other living organisms. It is to be understood that as used herein, the term "absorbable" is intended to be a generic term, which may also include implantable devices that are bioabsorbable, resorbable, bioresorbable, degradable or biodegradable in the living body or tissue. The term "absorbable" thus contrasts with the term "non-absorbable", which is meant for implantable devices that are permanently installed in the living body or tissue.

As used herein, the expression "multifilament suture" refers to a suture that includes a plurality of filaments that are combined together in a substantially random fashion, or that are combined together according to a twined pattern. The twined pattern can be according to a predetermined architecture. In some implementations, when the filaments that are combined together in a substantially random fashion, the filaments can be considered as being simply bundled together. In some implementations, when the twined pattern is according to a predefined architecture, the filaments can be organized in a twisted fashion.

As used herein, the term "twisted", can be considered to refer to an entwinement of two or more of the filaments into a cohesive structure. In some implementations, when the twined pattern is according to a predefined architecture, the filaments can be braided or interlaced, with some filaments crossing over other filaments. In addition, the expression "twined pattern" is intended to encompass implementations where a portion of the filaments are combined together, and optionally interlocked, to form a yarn, and selected yarns are subsequently combined according to the desired twined pattern. Thus, either filaments themselves can be twined, or interlaced, or yarns made of filaments can be twined.

In some implementations, when the twined pattern includes filaments or yarns crossing over each other, the twined pattern can be a one over one twined pattern, a one over two twined pattern, or a two over two twined pattern, for instance. It is to be understood that other types of twined patterns known in the art for producing multifilament sutures can also be suitable. In some implementations, the twined pattern can result in a multifilament suture having a predetermined number of twists per defined length such as, between about 10 and about 1,000 twists per meter of multifilament suture.

As specified above, the natural fibers for making the multifilament sutures and surgical meshes as described herein can have hydrophobic properties while being absorbable. The hydrophobic properties of the natural fibers can facilitate repelling or inhibiting fluid penetration into interstices defined between adjacent filaments or adjacent yarns of the multifilament suture used for forming the surgical suture or surgical mesh. The hydrophobic properties of the natural fibers can also facilitate preventing bacterial adherence onto the filaments of the multifilament suture used for forming the surgical suture or surgical mesh. These combined benefits can in turn contribute to preventing or reducing the formation of bacterial biofilms and thus surgical site infection. Although other types of natural fibers, and more specifically, natural fibers from a vegetable source, may have hydrophobic properties, these currently known natural fibers are non-absorbable. For instance, complete biodegradation of silk at physiological conditions is considered to occur two years after implantation. Silk is also known for inducing attachment of micro-organisms such as bacteria thereto, leading to inflammation. Examples of hydrophobic and non-absorbable natural fibers include for instance silk, which has been used extensively as a suture material to date.

Various implementations and features of the multifilament suture for use as a surgical suture and for producing surgical meshes will now be described in greater detail in the following paragraphs.

Multifilament Suture for a Surgical Suture

Figure 2:
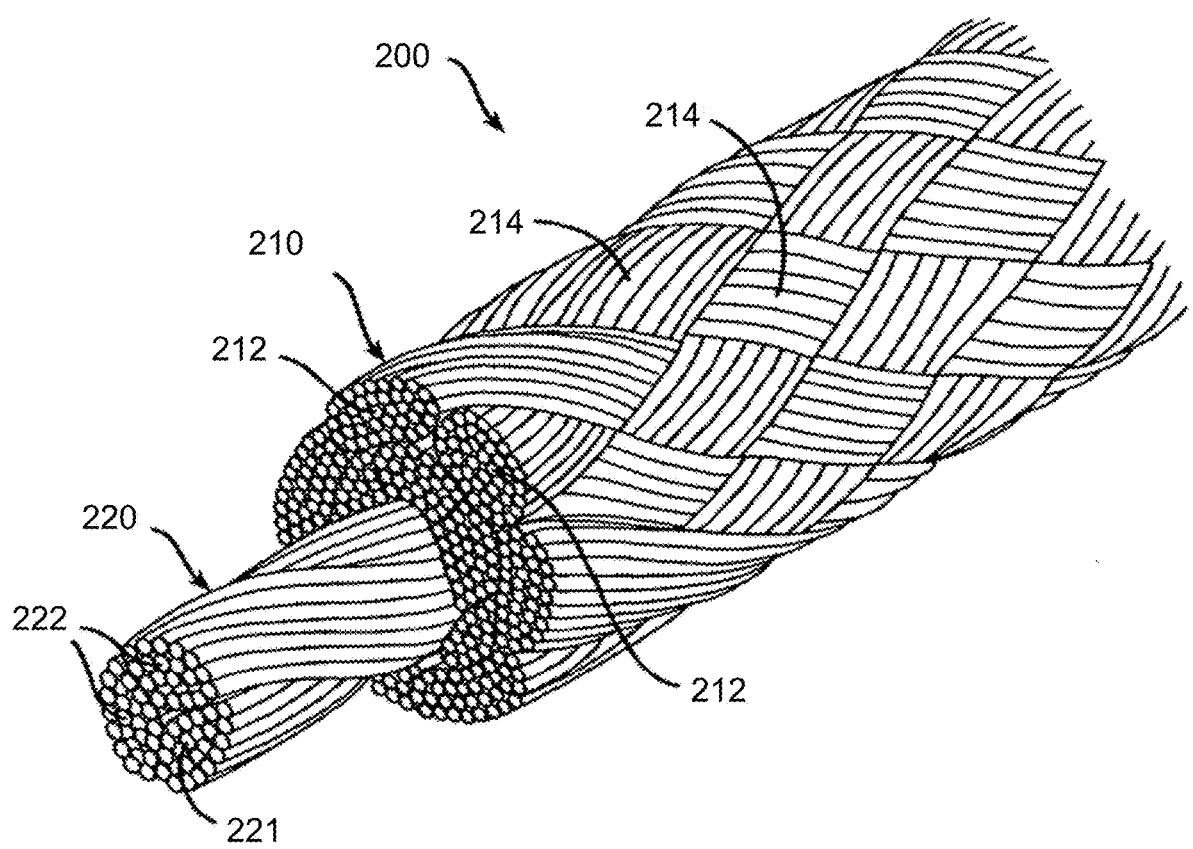
FIG. 2 is a perspective view of a multifilament suture, in accordance with another implementation.

Referring to FIG. 1, an exemplary implementation of a multifilament suture 100 is illustrated. In the illustrated implementation, the multifilament suture 100 includes a plurality of filaments 102 made of natural fibers, the filaments 102 being elongated and substantially continuous. The multiple filaments 102 are combined together according to a twined pattern, with the filaments 102 being slightly twisted without crossing over each other. Thus, it is to be understood that although the filaments 102 of the multifilament suture 100 shown in FIG. 1 are not crossing over each other, these filaments are still considered as being twisted since they are given a predefined architecture by twisting. Alternatively, and as mentioned above, the filaments can be combined together in a substantially random fashion, for instance in a bundle, or the filaments of the multifilament suture 100 can be provided according to any suitable twined pattern. For instance, in the implementation shown in FIG. 1, the filaments 102 are provided as standalone filaments of natural fibers, instead of a portion of the filaments being combined together to form yarns, such as shown in FIG. 2. When portions of filaments are combined together to form yarns, the yarns can subsequently be entwined according to the desired twined pattern, which can be for instance a one over one twined pattern, a one over two twined pattern, a two over two twined pattern, etc.

In the illustrated implementation, the multifilament suture 100 comprises forty intertwined filaments 102. It is to be understood that the multifilament suture 100 can comprise any other suitable number of filaments 102. For instance, in some implementations, the multifilament suture 100 can comprise one to two hundred filaments 102. Alternatively, the multifilament suture 100 can comprise forty to sixty filaments 102.

Referring now to FIG. 2, another implementation of a multifilament suture 200 is illustrated. In this implementation, the multifilament suture 200 includes a plurality of filaments 212 provided according to a twined pattern that defines a braided sheath 210 provided around a core 220. In this implementation, a first portion of the filaments are combined together to form a first yarn, a second portion of the filaments are combined together to form a second yarn and so on, and selected yarns of the first, second and so on yarns are subsequently braided according to the desired twined pattern to form the braided sheath 210. In the implementation shown, the twined pattern can be considered as corresponding to a one over one twined pattern. In the illustrated implementation, the yarns 214 of the braided sheath 210 have a substantially oval cross-section and includes multiple filaments 212 made of natural fibers that are longitudinally aligned with each other. In other implementations, the yarns 214 can have a circular, polygonal, or any other suitable cross-section and can be combined together differently than in the example shown. For instance, the filaments 212 can be provided according to the twined pattern shown in FIG. 1, with the filaments 212 being slightly twisted without crossing over each other.

Still referring to FIG. 2, the core 220 of the multifilament suture 200 includes multiple yarns 221 provided in a twined pattern that is slightly twisted. In the illustrated implementation, each yarn 221 includes a plurality of filaments 222 made of natural fibers as described herein. Alternatively, the yarn 221 can be a bundle of filaments combined together in any other way.

In some implementations, the multifilament suture 100, 200 can be configured to be sufficiently pliable to enable the formation of knots. The knots of multifilament suture 100, 200 can secure the multifilament suture 100, 200 to a surgical site to prevent, for instance, slipping of the multifilament suture 100, 200 following a surgical procedure and to maintain tension in the multifilament suture 100, 200. In such implementations, the multifilament suture 100, 200 can be independently secured to the surgical site, i.e., without additional implements such as a suture anchor or surgical clip, for a surgical procedure that involves approximating portions of tissue. In other implementations, the multifilament suture 100, 200 can be configured for use in cooperation with a suture anchor or a surgical clip.

One or more of the filaments 102, 212, 222 of the multifilament sutures 100, 200 are made of natural fibers having both absorbable properties and hydrophobic properties. More specifically, the filaments 102, 212, 222 of the multifilament sutures 100, 200 can have mechanical properties that are modified after a given period of time, which can correspond to a predetermined timepoint following a surgical procedure. Accordingly, the filaments 102, 212, 222 can adopt a modifiable configuration to degrade over time and therefore not require removal after healing at a surgical site has occurred.

In some implementations, the natural fibers can include cellulosic plant fibers such as milkweed fibers. The milkweed fibers can include at least one of *Asclepias syriaca* fibers and *Asclepias speciosa* fibers. It is to be understood that, in other implementations, the natural fibers can include milkweed fibers from other species of the genus *Asclepias*. In such implementations, the milkweed fibers of the intertwined filaments 102, 212, 222 can biodegrade naturally under physiological conditions while retaining their hydrophobic properties. The filaments 102, 212, 222 of the multifilament sutures 100, 200 made of milkweed fibers further have hydrophobic properties, which can facilitate repelling or inhibiting fluid penetration into interstices defined before adjacent filaments or adjacent yarns of the multifilament suture 100, 200. The hydrophobic properties of the filaments 102, 212, 222 provided by the milkweed fibers can further prevent bacterial adhesion thereto, which in turn can contribute to preventing surgical site infection.

In some implementations, at least a portion of the multifilament suture 100, 200 can be absorbed within an absorption period following a surgical procedure. As used herein, an "absorption period" refers to a period of time that results in a substantially complete absorption of the multifilament suture 100, 200 in a biological environment and, more specifically, the period of time for the filaments 102, 212, 222 to biodegrade via proteolysis or hydrolysis under physiological conditions. The absorption period can vary in accordance with various factors. Such factors can include, for instance, the number of filaments 102, 212, 222 of the multifilament suture 100, 200, a mean diameter of the multifilament suture 100, 200, the species of the natural fibers of the filaments 102, 212, 222, the type of surgical site and associated needed repair, the physiological characteristics of a patient and the physiological conditions at the site where the multifilament suture 100, 200 is to be implanted. In some implementations, the absorption period of the multifilament suture 100, 200 can be between about one week and about eight weeks, or between about two weeks and nine weeks, for instance. In other implementations, the multifilament suture 100, 200 can be configured such that the absorption period can be any other suitable period of time.

In some implementations, the filaments 102, 212, 222 of the multifilament sutures 100, 200 can include natural fibers from different sources. For instance, when the filaments include milkweed fibers, additional natural fibers that are different from milkweed fibers can be combined with the milkweed fibers to produce the filaments. The additional natural fibers can include for instance cellulosic plant fibers, or other types of natural fibers.

In some implementations, the additional natural fibers can include one or more natural fibers from the following group of natural fibres: kapok fibers, bamboo fibers, linen fibers, cotton fibers, abacá fibers, acetate fibers, banana fibers, coir fibers, flax fibers (used to make linen), hemp fibers, jute fibers, kenaf fibers, lyocell fibers, modal fibers, piña fibers, raffia fibers, ramie fibers, rayon fibers, sisal fibers, bast fibers, cedar bark fibers, esparto fibers, fique fibers, papyrus fibers, straw fibers, and soy protein fibers.

In some implementations, the additional natural fibers can include one or more natural fibers from the following group of natural fibres: spider silk fibers, wool fibers, alpaca fibers, angora wool fibers, azlon fibers, byssus fibers, camel hair fibers, cashmere wool fibers, chiengora fibers, lambswool fibers, llama fibers, mohair wool fibers, qiviut fibers, rabbit fibers, silk fibers, eri silk fibers, vicuña fibers, and yak fibers. Some of the above-listed natural fibers can also be referred to as animal fibres.

In some implementations, the additional natural fibers can have at least one property that makes them compatible for use with the other natural fibers forming the filaments. For instance, when the natural fibers of the filaments include milkweed fibers, the additional natural fibers, e.g., the cellulosic plant fibers, can be chosen to also be absorbable, and potentially hydrophobic as well.

In some implementations, the additional natural fibers can have at least one property complementing the properties of the natural fibers forming the filaments 102, 212, 222. For instance, when the natural fibers of the filaments include milkweed fibers, the additional natural fibers can be selected for their increased tensile strength relative to the natural fibers such as to improve the tensile properties of the filaments 102, 212, 222.

In other implementations, the multifilament suture 100, 200 can include a first set of filaments that are made of natural fibers, such as cellulosic plant fibers (e.g., milkweed fibers), and a second set of filaments that are made of natural fibers that are different from the natural fibers of the first set of filaments, or that are made from synthetic fibers (also referred to as a synthetic material or synthetic suture material) or mineral-based fibers. Once again, the natural fibers, the synthetic fibers or the mineral-based fibers of the second set of filaments can have at least one property that make them compatible for use with the natural fibers of the first set of filaments, for the intended use of the multifilament suture 100, 200. For instance, when the natural fibers of the first set of filaments include milkweed fibers, the natural fibers, the synthetic fibers or the mineral-based fibers of the second set of filaments can be chosen to also be absorbable, and potentially hydrophobic as well. Examples of synthetic materials that are absorbable include polyglactin, such as polyglactin 910 (Vicryl®), polyglycolic acid, polylactic acid, p-dioxanone, and trimethylene carbonate, for instance. In addition, the natural fibers, the synthetic fibers, or the mineral-based fibers of the second set of filaments can have at least one property complementing the properties of the natural fibers forming the filaments 102, 212, 222. For instance, when the natural fibers of the filaments include milkweed fibers, the natural fibers, the synthetic fibers, or the mineral-based fibers of the second set of filaments can be selected for their increased tensile strength relative to the natural fibers such as to improve the tensile properties of the filaments 102, 212, 222.

Additional examples of synthetic fibers than those provided above can include for instance polybutester, acrylic fibers, Kevlar™ fibers, modacrylic fibers, Nomex™ fibers, nylon fibers, polyester fibers, spandex fibers, and rayon fibers.

Examples of mineral-based fibers can include for instance glass fibers (e.g., boron trioxide glass-based fibers such as those described in U.S. Pat. No. 8,173,154, which is incorporated herein by reference in its entirety, $CaO$—$B_2O_3$—$SiO_2$ glass fibers and borate glass 13-93B3) and fiberglass fibers.

Accordingly, the multifilament suture 100, 200 can include filaments 102, 212, 222 that are made of different suture materials. Thus, in some implementations, the multifilament suture 100, 200 can include a first set of filaments comprising natural fibers being both absorbable and hydrophobic at physiological conditions, and a second set of filaments comprising an absorbable synthetic suture material, the first and second set of filaments being combined together according to a twined pattern to form the multifilament suture.

Although one of the overall objectives of the multifilament suture 100, 200 described herein is to be absorbable, it is contemplated that in alternative implementations, the second set of the filaments 102, 212, 222 can include synthetic fibers, mineral-based fibers or natural fibers that may be non-absorbable, depending on the clinical scenario and associated medical needs for which the multifilament suture is intended to be used.

In some implementations, one or more of the filaments 102, 212, 222 of the multifilament suture 100, 200 can be made of any type of fiber or combination of fibers selected from the natural fibers, the synthetic fibers, and the mineral-based fibers described herein. As mentioned above, examples of natural fibers can include milkweed fibers, kapok fibers, bamboo fibers, linen fibers, cotton fibers, abacá fibers, acetate fibers, banana fibers, coir fibers, flax fibers, hemp fibers, jute fibers, kenaf fibers, lyocell fibers, modal fibers, piña fibers, raffia fibers, ramie fibers, rayon fibers, sisal fibers, bast fibers, cedar bark fibers, esparto fibers, fique fibers, papyrus fibers, straw fibers, and soy protein fibers, spider silk fibers, wool fibers, alpaca fibers, angora wool fibers, azlon fibers, byssus fibers, camel hair fibers, cashmere wool fibers, chiengora fibers, lambswool fibers, llama fibers, mohair wool fibers, qiviut fibers, rabbit fibers, silk fibers, eri silk fibers, vicuña fibers, and yak fibers. Some of the above-listed natural fibers can also be referred to as animal fibres. Examples of synthetic fibers can include polybutester, acrylic fibers, Kevlar™ fibers, modacrylic fibers, Nomex™ fibers, nylon fibers, polyester fibers, spandex fibers, and rayon fibers. Examples of mineral-based fibers can include glass fibers such as boron trioxide glass-based fibers, $CaO$—$B_2O_3$—$SiO_2$ glass fibers and borate glass 13-93B3, and fiberglass fibers. In some implementations, the filaments 102, 212, 222 can include a single type of fiber, such as a single type of fiber selected from the group of natural fibers, synthetic fibers and mineral-based fibers, or a combination of fibers selected from the group of natural fibers, synthetic fibers and mineral-based fibers and having at least one complementary property relative to each other. In such implementations, the composition or the nature of the filaments can be chosen such that the resulting multifilament suture is suitable for a clinical scenario or the associated medical needs for which the multifilament suture 100, 200 is intended to be used. Is it thus to be understood that in some implementations, the filaments of the multifilament suture may not include cellulosic plant fibers such as milkweed fibers.

The multifilament suture 100, 200 is configured to have a suitable tensile strength for a surgical procedure such as, for instance, to enable the multifilament suture 100, 200 to be knotted and secured to a surgical site. The tensile strength of the multifilament suture 100, 200 is defined in part by a diameter of the multifilament suture 100, 200. In some implementations, the multifilament suture 100, 200 can have a diameter between about 0.01 mm and about 0.7 mm, or between about 0.1 mm and about 0.5 mm. Alternatively, the multifilament suture 100, 200 can have any other diameter providing a suitable tensile strength.

In some implementations, the multifilament suture 100, 200 can include a biocompatible coating. The biocompatible coating can be deposited onto an external surface of the multifilament suture 100, 200, or onto an external surface of the filaments 102, 212, 222. In some implementations, the biocompatible coating can contribute to providing an outer surface of the multifilament suture 100, 200 that is smoother, i.e., more "slippery", compared to when no coating would be used. Providing a multifilament suture 100, 200 with a smoother external surface can be beneficial for instance for reducing the friction generated by the multifilament suture 100, 200 when passing through tissue, which can also be referred to as "tissue-drag". In some implementations, the reduction in tissue-drag can be the result of the biocompatible coating having a thickness that is sufficient to substantially reduce or eliminate irregularities in an outer surface of the multifilament suture 100, 200 such as, for instance, protuberances associated with the interstices formed between the filaments 102, 212. In some implementations, the biocompatible coating can be bonded to the external surface of the multifilament suture 100, 200, without necessarily penetrating the interstices defined between adjacent filaments 102, 212. The biocompatible coating can further be deposited onto the outer surface of the multifilament suture 100, 200 to prevent peeling, stripping or separation thereof during a surgical procedure.

In some implementations, the biocompatible coating can include silicone. In some implementations, a biocompatible coating that includes silicone can contribute to extend the absorption period of the multifilament suture 100, 200. In some implementations, the biocompatible coating that includes silicone can provide an outer surface of the multifilament suture 100, 200 that can resist deleterious modifications under physiological conditions, and also can result in a multifilament suture having a smoother external surface compared to when silicone would not be present in the biocompatible coating. As mentioned above, providing a multifilament suture with a smooth external surface can contribute to reducing tissue-drag of the multifilament suture 100, 200 when passing through tissue. In some implementations, a biocompatible coating including silicone can also reduce potential adverse or undesirable interaction with blood present in the vicinity of the multifilament suture, such as, encrustation of blood on the external surface of the multifilament suture 100, 200.

In some implementations, the thickness of the biocompatible coating can average at least a quarter of a diameter of the filaments 102, 212. In other implementations, the thickness of the biocompatible coating can average at least a half of the diameter of the filaments 102, 212.

The biocompatible coating can be made of an absorbable material such as, for instance, an absorbable polymer. In some implementations, the biocompatible coating can be made of an absorbable material having antibacterial or antifungal properties. Examples of biocompatible coatings can include poloxamer 188 and calcium stearate, among others.

In some implementations, the biocompatible coating can include a bioactive agent having therapeutic properties and configured to induce or facilitate a desired biological response. The bioactive agent can include, for instance, a cell growth promoter, a cell growth inhibitor, an antibiotic, a cytokine, a healing promoter, a clotting modulator, an anti-inflammatory, and an anti-scarring agent. In some implementations, the bioactive agent can include an osteoconductive bone adhesive, calcium carbonate, fatty acids, a lubricant, and/or an antiseptic chemical. In some implementations, the bioactive agent can be combined with the filaments 102, 212, 222 other than via a biocompatible coating.

In some implementations, the filaments 102, 212, 222 of the multifilament suture 100, 200 can be subjected to a chemical treatment to produce chemically treated filaments. In some implementations, the chemical treatment can be chosen to modify one or more properties of the filaments 102, 212, 222. Examples of such properties can include the tensile strength, the susceptibility of the chemically treated filaments to trigger an inflammation reaction, the speed at which the chemically treated filaments are absorbed, and the biocompatibility, to name a few. For instance, the chemical treatment can be chosen to produce chemically treated filaments having a higher tensile strength for clinical applications where a reduced susceptibility of the multifilament suture breaking is sought after. In some implementations, the chemical treatment can be chosen to sterilize the filaments 102, 212, 222 and can include, for instance, subjecting the multifilament suture to gas sterilization using ethylene oxide. Thus, it is to be understood that the filaments 102, 212, 222 are configured to be sterilized to produce sterile filaments 102, 212, 222 and a sterile multifilament suture 100, 200.

Suture Device

In some implementations, there is provided a suture device that includes a multifilament suture 100, 200 as described herein, and a suture needle. The suture needle includes a needle point configured for penetrating a biological tissue, and a suture engaging end configured to be engaged with the multifilament suture, via a releasable engagement or a fixed engagement. The releasable engagement of the suture needle can be for instance an eye attachment. The fixed engagement of the suture can be for instance via a swaged end. The swaged end is configured to receive an extremity of the multifilament suture 100, 200 within the hollow body of the suture needle, which is subsequently crimped to fix the extremity of the multifilament suture therein. In other implementations, the multifilament suture 100, 200 can be frictionally or adhesively secured to the suture engaging end of the needle. The suture needle can be any type of suture needle as known in the art, and can have for instance a straight body, a curved body, a serpentine body, or a body having any other suitable shape.

Multifilament Suture for a Surgical Mesh

Figure 3:
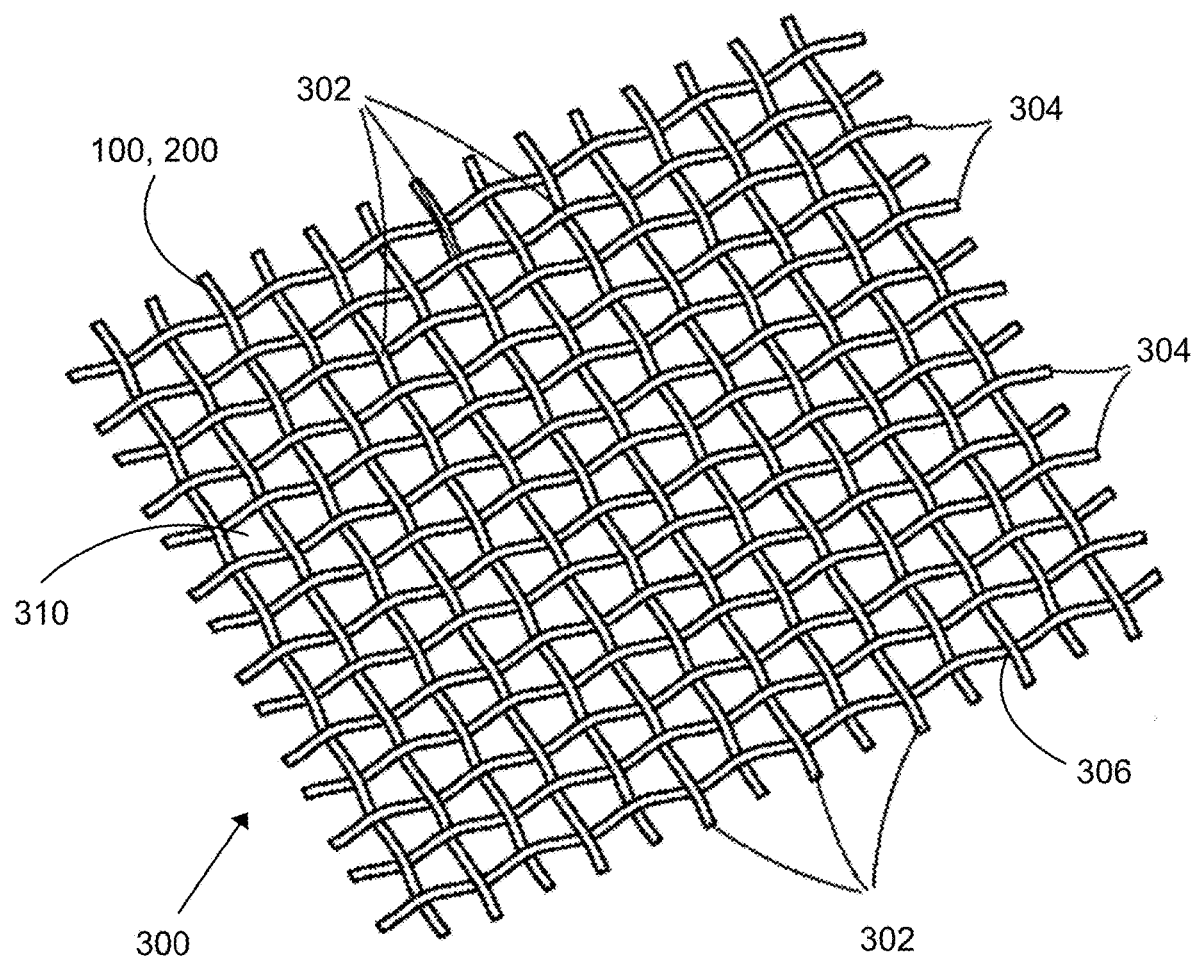
FIG. 3 is a perspective view of a surgical mesh, in accordance with an implementation.
Figure 4A:
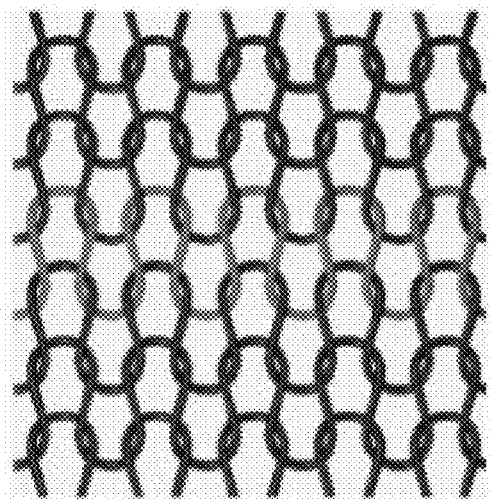
FIG. 4A is a top plan view of a surgical mesh including filaments provided in a knitted pattern, in accordance with an implementation.
Figure 4B:
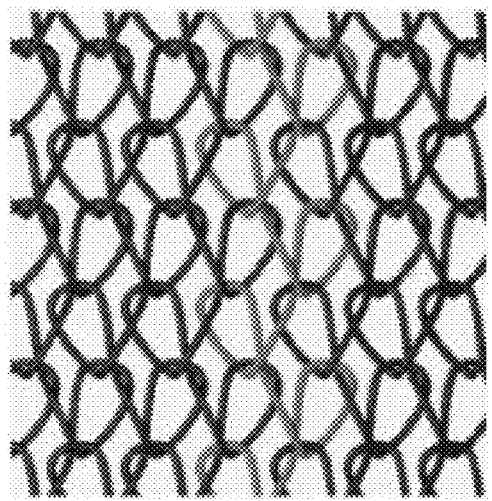
FIG. 4B is a top plan view of a surgical mesh including filaments provided in a warp-knitted pattern, in accordance with an implementation.
Figure 4C:
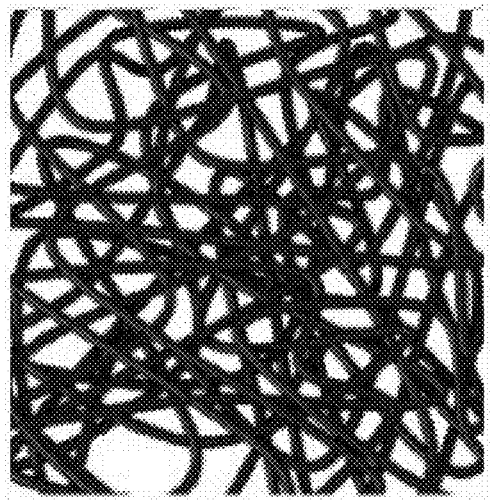
FIG. 4C is a top plan view of a surgical mesh including filaments provided in a nonwoven pattern, in accordance with an implementation.
Figure 4D:
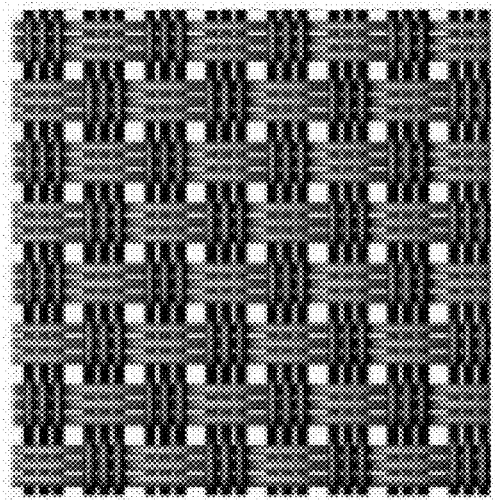
FIG. 4D is a top plan view of a surgical mesh including filaments provided in a woven pattern, in accordance with an implementation.

Referring now to FIG. 3, an exemplary implementation of a surgical mesh 300 is illustrated. The surgical mesh 300 can provide a porous matrix for the reinforcement, support and/or repair of hard tissue or soft tissue during the healing process or during surgeries. This includes, but is not limited to, defects of the thoracic wall, suture line reinforcement, muscle flap reinforcement, hernia repair, soft tissue reconstructive procedures including plastic and reconstructive surgical applications, and for reinforcement of soft tissues which are repaired by suture or suture anchors. The porous matrix of the surgical mesh 300 can allow tissue infiltration to incorporate the surgical mesh 300 to facilitate regeneration of tissue in a body cavity such as, for instance, an opening in an abdomen.

In the illustrated implementation, the surgical mesh 300 includes a plurality of filaments 102, 212, 222 as described herein, the filaments being provided spaced-apart from each other and crossed over and under each other in an alternating pattern at intersection points 306, such that the twined pattern corresponds to a mesh pattern. The filaments include natural fibers having both absorbable properties and hydrophobic properties such as, for instance, milkweed fibers. In some implementations, the filaments can be configured as multifilament sutures 100, 200 as described herein. Accordingly, the surgical mesh 300 can have mechanical properties that are modified after a given period of time such as to not require removal after healing at a surgical site has occurred, while preventing or reducing bacterial adhesion to the surgical mesh 300 and formation of bacterial biofilms and thus surgical site infection.

For instance, in some implementations, the mesh pattern of the surgical mesh 300 can be a knitted pattern, a warp-knitted pattern, a nonwoven pattern, a woven pattern, or a combination thereof. An example of each of a knitted pattern, a warp-knitted pattern, a nonwoven pattern and a woven pattern is shown in FIGS. 4A to 4D, respectively. Additional examples of a warp-knitted pattern that can be suitable as a mesh pattern for the surgical mesh 300 are disclosed in Table 1 of Liu et al., RSC Adv., 2019, 9, 17679, which is incorporated herein by reference in its entirety. It is to be understood that other types of mesh patterns can also be suitable, and that the above examples are given for exemplary purposes only.

Referring back to FIG. 3, the surgical mesh 300 includes a plurality of first multifilament sutures 302 extending along a first direction of the surgical mesh, and a plurality of second multifilament sutures 304 extending along a second direction of the surgical mesh, the second direction being different than the first direction. In the illustrated implementation, the first multifilament sutures 302 intersect the second multifilament sutures 304 at a substantially perpendicular angle. It is to be understood that, in other implementations, the plurality of first multifilament sutures 302 can intersect the plurality of second multifilament sutures 304 at an acute or an obtuse angle.

The woven pattern of the first and second multifilament sutures 302, 304 define voids 310, into which cells of the biological tissue where the surgical mesh is implanted can migrate and proliferate. The migration and proliferation of the cells of hard tissue or soft tissue can thus contribute to promoting growth of the hard tissue or soft tissue around the porous matrix of the surgical mesh 300. The distance between adjacent first and second multifilament sutures 302, 304 define the sizing of the voids 310. In some implementations, the distance between adjacent first and second multifilament sutures 302, 304 can thus be reduced to reduce the size of the voids 310 and provide a denser mesh, which can result in a less permeable mesh if desired.

In some implementations, the surgical mesh 300 can include a plurality of mesh layers. When the surgical mesh 300 includes a plurality of mesh layers, the mesh layers can be multiple layers of the surgical mesh as described above, or the mesh layers can include at least some mesh layers made of a different material than the multifilament sutures as described herein. In addition, the configuration of the first and second multifilament sutures 302, 304 can remain constant or be varied between layers. For instance, the sizing of the voids 310 and/or the angle between adjacent ones of the first and second multifilament sutures 302, 304 can be varied between mesh layers of the surgical mesh 300.

In some implementations, the first and second multifilament suture 302, 304 of the surgical mesh 300 can include a bioactive agent having therapeutic properties and configured to induce or facilitate a desired biological response. For instance, in some implementations, the first and second multifilament suture 302, 304 can include an anti-microbial substance or antibiotic active against bacteria within an infected surgical site to promote healing. In other implementations, the first and second multifilament suture 302, 304 can include a cell growth promoter, a cytokine, a healing promoter, a clotting modulator, or an anti-inflammatory agent to promote a healing of the surgical site.

In other implementations, the surgical mesh 300 can be implanted at a surgical site that is already infected to facilitate a healing response. Given the hydrophobic properties of the filaments forming the first and second multifilament suture 302, 304 of the surgical mesh 300 and as described above, the first and second multifilament suture 302, 304 can enable avoiding adhesion of the bacteria to the filaments and the additional proliferation of bacteria at the surgical site that could potentially occur with another type of surgical mesh that would not include hydrophobic filaments, thereby facilitating the healing of the infected surgical site. The hydrophobic properties of the filaments forming the first and second multifilament suture 302, 304 of the surgical mesh 300 can thus be considered as having an intrinsic antibacterial activity that can make them suitable for use in applications where a pre-existing infection is present at the surgical site.

In the illustrated implementation, the surgical mesh 300 is shown as having a substantially square shape extending about a substantially common plane. In other implementations, the surgical mesh can have any other suitable shape, which can be determined according to its intended medical use. For instance, in some implementations, the surgical mesh can take the form of a corrugated surgical mesh comprising a series of undulating grooves and ridges. In some implementations, the surgical mesh 300 can be further combined with non-mesh materials such as, for instance, rods, fillers to form a surgical scaffold having a desired shape and structural strength. Such surgical scaffold can be used for instance to reinforce soft tissue where defects or weakness exist and provide support for internal organs, and to treat surgical or traumatic wounds, among other applications.

To provide a more concise description, some of the quantitative expressions provided herein are qualified with the term "about". It will be understood that whether the term "about" is used explicitly or not, every quantity recited herein is meant to refer to an actual given value, and it is also meant to refer to the approximation to such given value that would reasonably be inferred by a person of ordinary skill in the art, including approximations due to the experimental and/or measurement conditions for such given value.

Several alternative embodiments and examples have been described and illustrated herein. The embodiments of the invention described above are intended to be exemplary only. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the central characteristics thereof. The present examples and embodiments, therefore, are to be considered in all respects as illustrative and not restrictive, and the invention is not to be limited to the details given herein. Accordingly, while the specific embodiments have been illustrated and described, numerous modifications come to mind. The scope of the invention is therefore intended to be limited solely by the scope of the appended claims.

The invention claimed is:

1. A multifilament suture for use as a surgical suture, the multifilament suture comprising:
   a plurality of filaments combined together according to a twined pattern, at least one filament of the plurality of filaments comprising natural fibers, the natural fibers being both absorbable and hydrophobic at physiological conditions.

2. The multifilament suture of claim 1, wherein the natural fibers comprise cellulosic plant fibers.

3. The multifilament suture of claim 2, wherein the cellulosic plant fibers comprise milkweed fibers.

4. The multifilament suture of claim 3, wherein the milkweed fibers include one or more of *Asclepias SYRIACA* fibers and *Asclepias speciosa* fibers.

5. The multifilament suture of claim 3, wherein the plurality of filaments further comprises additional natural fibers that are different from the milkweed fibers.

6. The multifilament suture of claim 5, wherein the additional natural fibers comprise cellulosic plant fibers.

7. The multifilament suture of claim 1, wherein the plurality of filaments further comprises absorbable synthetic fibers.

8. The multifilament suture of claim 1, further comprising a biocompatible coating provided onto an external surface of the multifilament suture.

9. The multifilament suture of claim 8, wherein the biocompatible coating is configured to reduce tissue-drag of the multifilament suture.

10. The multifilament suture of claim 8, wherein the biocompatible coating comprises a bioactive agent having therapeutic properties.

11. The multifilament suture of claim 1, wherein the biocompatible coating comprises an absorbable polymer.

12. A suture device for approximating portions of a biological soft tissue, the suture device comprising:
   the multifilament suture of claim 1; and
   a suture needle having a needle point configured for penetrating tissue, and a suture engaging end configured for engagement with the multifilament suture.

13. A surgical mesh for implantation at a surgical site, the surgical mesh comprising:
   a plurality of multifilament sutures each comprising a plurality of filaments as defined in claim 1, the plurality of multifilament sutures being combined together according to a mesh pattern.

14. The surgical mesh of claim 13, wherein the natural fibers comprise cellulosic plant fibers.

15. The surgical mesh of claim 14, wherein the cellulosic plant fibers comprise milkweed fibers.

16. The surgical mesh of claim 15, wherein the milkweed fibers include one or more of *Asclepias syriaca* fibers and *Asclepias speciosa* fibers.

17. The surgical mesh of claim 15, wherein the plurality of filaments further comprises additional natural fibers that are different from the milkweed fibers.

18. The surgical mesh of claim 17, wherein the additional natural fibers comprise cellulosic plant fibers.

19. The surgical mesh of claim 13, wherein the plurality of filaments further comprises absorbable synthetic fibers.

20. The surgical mesh of claim 13, wherein the surgical mesh defines a porous matrix configured to promote tissue growth at the surgical site.

21. The surgical mesh of claim 13, further comprising a non-mesh material, the combination of the surgical mesh and the non-mesh material forming a surgical scaffold configured to provide support for tissue surrounding the surgical site.

22. A suture device for approximating portions of a biological soft tissue, the suture device comprising:
   a multifilament suture comprising:
      a plurality of filaments combined together according to a twined pattern, at least one filament of the plurality of filaments comprising milkweed fibers; and
   a suture needle having a needle point configured for penetrating tissue, and a suture engaging end configured for engagement with the multifilament suture.

* * * * *